(12) United States Patent
Taheri (10) Patent No.: US 6,659,950 B2
(45) Date of Patent: Dec. 9, 2003

(54) PERCUTANEOUS EPICARDIAL INJECTION

(76) Inventor: Syde Taheri, 1275 Delaware Ave., Buffalo, NY (US) 14209

( * ) Notice: Subject to any disclaimer, the term of this patent is extended or adjusted under 35 U.S.C. 154(b) by 0 days.

(21) Appl. No.: 09/835,305

(22) Filed: Apr. 12, 2001

(65) Prior Publication Data

US 2002/0151868 A1 Oct. 17, 2002

Related U.S. Application Data

(60) Provisional application No. 60/272,323, filed on Mar. 2, 2001.

(51) Int. Cl.[7] ............................. A61B 8/12; A61M 31/00
(52) U.S. Cl. ...................... 600/439; 604/509; 604/510; 600/467
(58) Field of Search ................................. 606/1, 10–17; 600/439, 466–467, 664–665, 387, 476, 478; 607/13–17, 89, 122; 604/20, 48, 509, 510

(56) References Cited

U.S. PATENT DOCUMENTS

| | | | | |
|---|---|---|---|---|
| 5,591,159 A | * | 1/1997 | Taheri | 606/15 |
| 5,607,421 A | * | 3/1997 | Jeevanandam et al. | 606/15 |
| 5,725,523 A | * | 3/1998 | Mueller | 606/15 |
| 6,171,303 B1 | * | 1/2001 | Ben-Haim et al. | 606/15 |
| 6,176,855 B1 | * | 1/2001 | Heckele et al. | 606/15 |
| 6,199,554 B1 | * | 3/2001 | Mann et al. | 128/898 |
| 6,258,083 B1 | * | 7/2001 | Daniel et al. | 606/15 |

* cited by examiner

Primary Examiner—Francis J. Jaworski
(74) Attorney, Agent, or Firm—Walter W. Duft (57) ABSTRACT

A percutaneous epicardial injection apparatus for myocardial repair and treatment includes a catheter having a tubular wall, an interior portion surrounded by the tubular wall, a base end, a distal end, and a central longitudinal axis extending between the catheter base end and the catheter distal end. The catheter distal end has an end face that is formed at an oblique angle relative to the catheter longitudinal axis and adapted to attach to a patient's myocardium using suction. A lumen extends from the catheter base end to the catheter distal end within the catheter interior. The lumen is adapted to slidably support an elongated syringe having a needle tip adapted for movement between a retracted position wherein the needle tip is recessed within the catheter interior to an extended position wherein the needle tip extends from the catheter interior. The injection apparatus may be used to introduce a myocardial repair or treatment material into a dysfunctional area of the myocardium while the catheter distal end is attached thereto by extending the needle tip into the myocardium and injecting the myocardial repair or treatment material into the dysfunctional area.

18 Claims, 13 Drawing Sheets

PERCUTANEOUS EPICARDIAL INJECTION

CROSS-REFERENCE TO RELATED APPLICATIONS

This application claims the benefit of U.S. Provisional Application No. 60/272,323, filed on Mar. 2, 2001.

STATEMENT REGARDING FEDERALLY SPONSORED RESEARCH OR DEVELOPMENT

Not Applicable

BACKGROUND OF THE INVENTION

1. Field of the Invention

This invention relates to cardio myopathy and the treatment thereof.

2. Description of the Prior Art

By way of background, cardio myopathy, as caused for example by myocardial infarction, is a common disorder. Twenty thousand new cases are reported yearly in the United States and 25–50% of such cases will result in death after three years. The problem is that damaged adult heart muscle does not regenerate and myocardial functionality cannot be restored using the body's natural healing mechanisms. The myocardium tends to dilate and areas of the ventricular walls may become hypokinetic, or even akinetic, such that congestive heart failure often develops in affected individuals.

Previous medical techniques have not substantially reduced the morbidity or mortality of this condition. Past efforts in this area include removing autologous muscle cells, stem cells, etc., and culturing them to generate the large number of implantation cells necessary for myocardial repair. The cultured cells are then implanted via injection into the myocardium, where they have an opportunity to regenerate new heart muscle. Applicant has previously proposed a cell patch method whereby autologous muscle grafts are applied to damaged myocardial tissue. See U.S. Pat. No. 5,327,913. According to this method, the muscle grafts are placed against a patient's outer myocardial wall and a section of the patient's greater omentum is applied over the grafts to supply blood to the transplanted tissue. In a recently developed improvement of the cell patch method, a percutaneous procedure is used to secure the muscle grafts to the myocardium. Applicant has also recently proposed a microgranule treatment wherein autologous myocyte microgranules are injected into a patient's inner or outer myocardial wall using an injection needle introduced via a transfemoral or surgical approach. According to a further recent proposal by Applicant, a cradle-assisted myocardial repair and treatment method uses a cradle designed for engagement with the myocardium and injection of a myocyte donor material therein. In one cradle embodiment, the cradle is introduced via a transarterial-endocardial approach and is inflated within a ventricle to engage the endocardial wall. In another cradle embodiment, the cradle is introduced percutaneously via an epicardial approach and is adapted to wrap around a portion of the outer myocardial wall. In each of the foregoing cradle embodiments, the cradle supports injection needles for injecting a desired material into the myocardium.

Evaluation of the various treatment proposals outlined above suggests a need for a more efficient method of applying myocyte donor (or other) material to the myocardium. For example, transcavitary myocardial injection of material requires arterial puncture and a needle carrier to deliver cells or drugs into the myocardium. In addition, X-ray imaging has to be available to guide the needle into the proper position. The cradle assisted myocardial repair proposal described above makes use of a percutaneous approach in one of its embodiments and thus has many advantages over transcavitary procedures. However, the cradle-assisted proposal may not be optimal for all myocardial repair and treatment scenarios and applicant believes that further improvements in myocardial repair and treatment may therefore be realized.

SUMMARY OF THE INVENTION

The foregoing problems are solved and an advance in the art is obtained by a novel apparatus for percutaneous epicardial injection. The injection apparatus includes a catheter having a tubular wall, an interior portion surrounded by the tubular wall, a base end, a distal end, and a central longitudinal axis extending between the catheter base end and the catheter distal end. The catheter distal end has an end face oriented at an oblique angle relative to the catheter longitudinal axis and is adapted to attach to a myocardium using suction. A lumen extends from the catheter base end to the catheter distal end within the catheter interior. The lumen is adapted to slidably support an elongated syringe having a needle tip adapted for movement between a retracted position wherein the needle tip is recessed within the catheter interior to an extended position wherein the needle tip extends from the catheter interior. The injection apparatus may be used to introduce a myocardial repair or treatment material into a dysfunctional area of the myocardium while the catheter distal end is attached thereto by extending the needle tip into the myocardium and injecting the myocardial repair or treatment material into the dysfunctional area.

The catheter distal end is provided with suction elements that are adapted to facilitate the aforementioned suction attachment of the catheter to the myocardium. The suction elements may include a plurality of openings located in spaced relation around the tubular wall end face. In a modified construction, a soft tubular ring member is mounted at the catheter distal end. The ring member has a plurality of openings located in spaced relation around an exposed face of the tube that provide the suction elements. In either construction, the suction elements can be respectively connected to plural corresponding vacuum passages that extend in the tubular wall from the catheter distal end to the catheter base end. Alternatively, the suction elements can be connected to a single vacuum passage that extends to the catheter base end.

The percutaneous epicardial injection apparatus of the invention may further include a second lumen extending from the catheter base end to the catheter distal end within the catheter interior, and carrying an optical imaging device and light source. A third lumen may likewise be provided for carrying an ultrasound probe. In a further alternative implementation of the invention, a cell counter can be mounted on the tubular wall for monitoring repair cell introduction into the myocardium. A pair of electrodes can also be mounted at the catheter distal end for EKG monitoring or the like.

The catheter interior can be either hollow or solid filled. If the catheter interior is hollow, the catheter will preferably include a cover member mounted on the tubular wall at the catheter distal end. The cover member is perforated to receive the various lumena. If the catheter interior is solid filled, it will be perforated with passages extending between the catheter distal end and the catheter base end to provide the lumena, or to receive separate tubes that provide the lumena.

In addition to the above-summarized percutaneous epicardial injection apparatus, the invention further contemplates a procedure for applying a myocardial repair or treatment material to a patient's myocardium. This procedure is initiated by inserting via percutaneous approach beneath the xiphoid bone of a patient, a small needle into the patient's pericardium. A guide wire and balloon dilator are then introduced into the patient's pericardial sac and the pericardial sac is dilated. Following elevation of the patient's heart (as necessary), the medical practitioner selects the percutaneous epicardial injection apparatus of the invention and prepares it for use. The catheter is introduced into the patient using the previously formed sub-xiphoidal opening and guided into the pericardial sac. Advantageously, the catheter can be self-guided to the selected area without X-ray imaging using the optical imaging system summarized above. Moreover, the above-summarized ultrasound imaging device can be used to appraise ventricular motility. When the selected area is identified, the catheter distal end is attached to the myocardium with the aid of its oblique tubular wall end face and associated suction elements. The needle tip of the syringe may now be extended into the selected area and the repair or treatment material may be injected into the myocardium.

BRIEF DESCRIPTION OF THE DRAWING

The foregoing and other features and advantages of the invention will be apparent from the following more particular description of preferred embodiments of the invention, as illustrated in the accompanying Drawing, in which.

DETAILED DESCRIPTION OF THE PREFERRED EMBODIMENT

Figure 1:
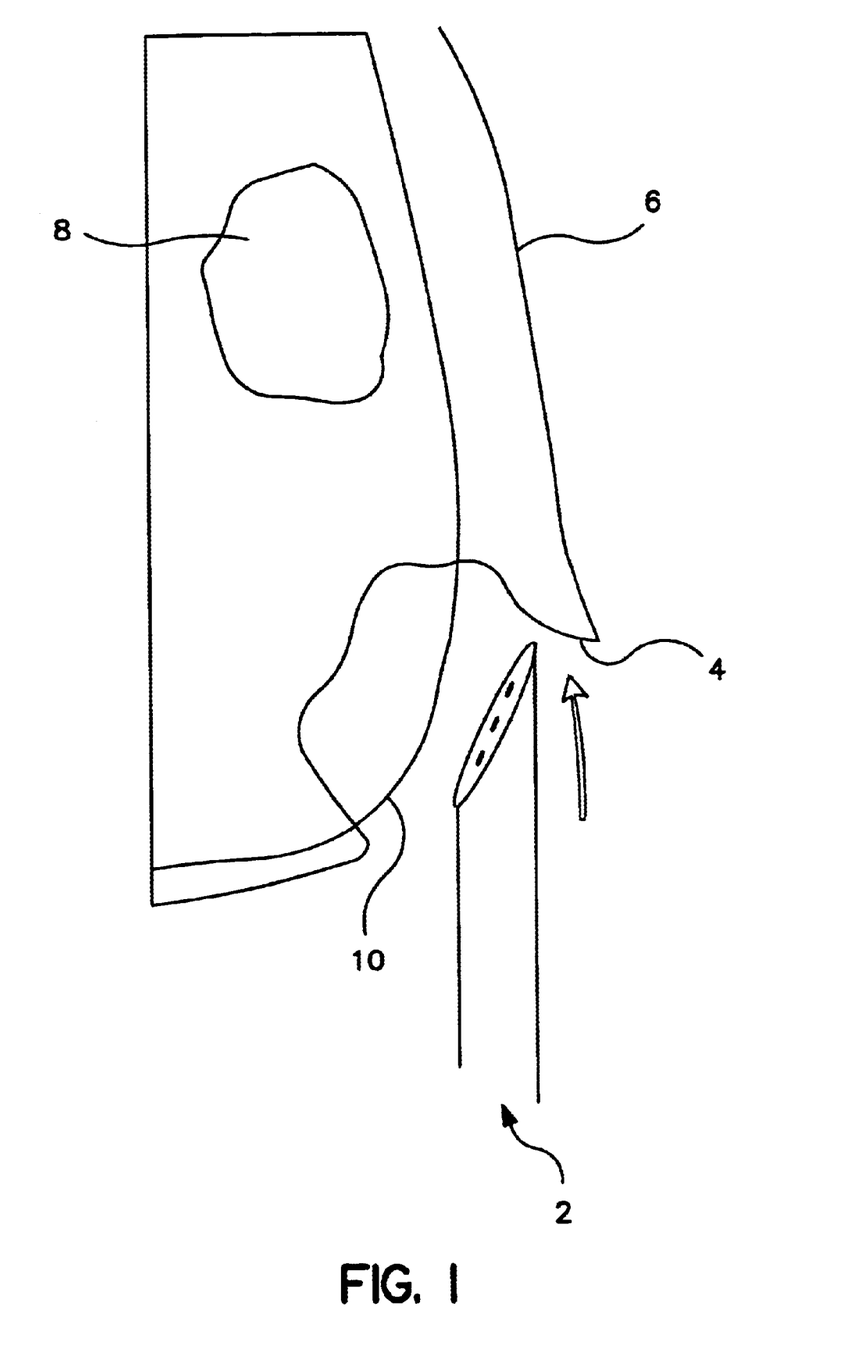
FIG. 1 is a perspective view of the distal end portion of a percutaneous epicardial injection apparatus constructed in accordance with the invention, showing the apparatus entering an opening in a dilated pericardial sac to treat a damaged myocardial area.

The percutaneous epicardial injection apparatus of the invention will now be described by way of exemplary embodiments shown by the drawing figures, in which like reference numerals indicate like elements in all of the several views. Thus, turning to FIG. 1, a percutaneous epicardial injection apparatus 2 is positioned to enter through an opening 4 in a patient's pericardial sac 6 in order to reach a damaged area 8 of the patient's myocardium 10. As more clearly shown in FIGS. 2–5B, the injection apparatus 2 includes a catheter 12 having a tubular wall 14, an interior portion 16 surrounded by the tubular wall 14, a base end 18, a distal end 20, and a central longitudinal axis 22 extending between the catheter base end 18 and the catheter distal end 20. The catheter distal end 20 is adapted to attach to the myocardium 10 via suction, as described in more detail below. The catheter 12 can be made from any suitable bio-compatible polymer that is flexible yet stiff enough to facilitate percutaneous introduction thereof into a patient. Polypropylene tubing is one exemplary material that could be used to provide the requisite combination of flexibility and stiffness. However, because the catheter 12 is designed to attach to the myocardium 10 via suction, the catheter distal end 20 should be made sufficiently soft and compliant to enable it to conform to the surface of the myocardium 10. Alternatively, a separate soft and compliant tubular ring member (see below) can be mounted at the catheter distal end 20.

Figure 2:
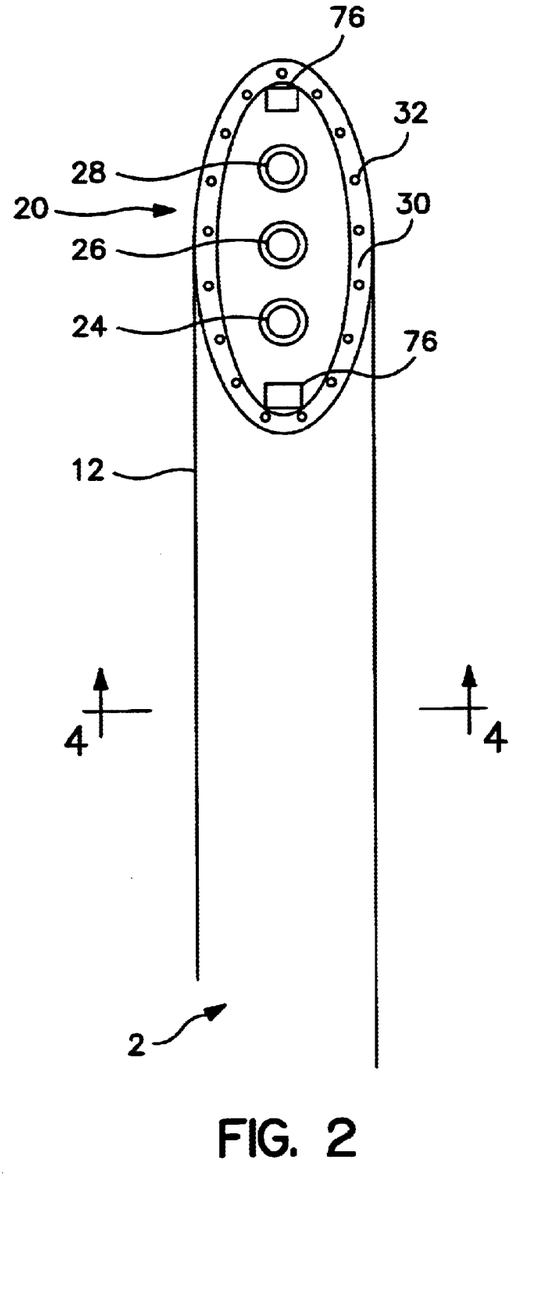
FIG. 2 is a front elevational view of the distal end portion of the injection apparatus of FIG. 1, showing the face of the distal tip thereof.
Figure 3:
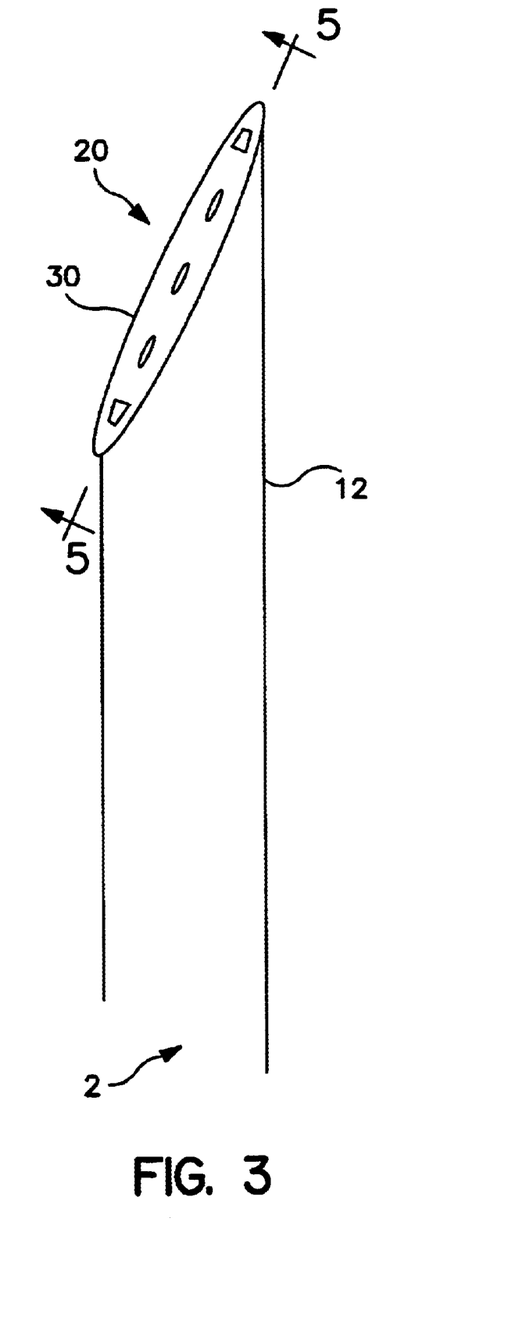
FIG. 3 is a perspective view of the distal end portion of the injection apparatus of FIG. 1, showing the oblique slope of the distal tip end thereof.
Figure 5A:
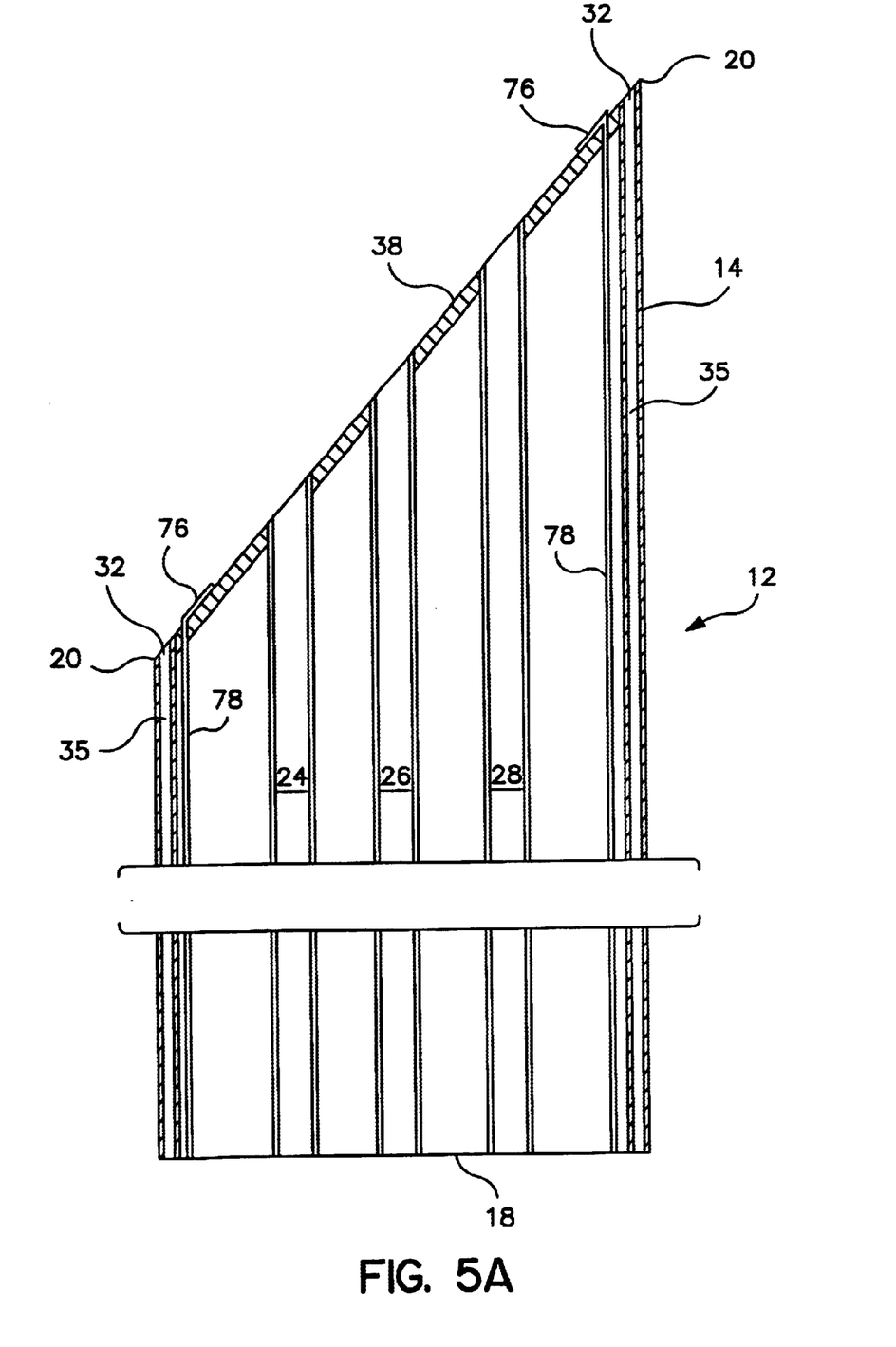
FIG. 5A is a cross-sectional view taken along substantially along line 5—5 in FIG. 3 and showing a first alternative construction of the catheter distal end.
Figure 5B:
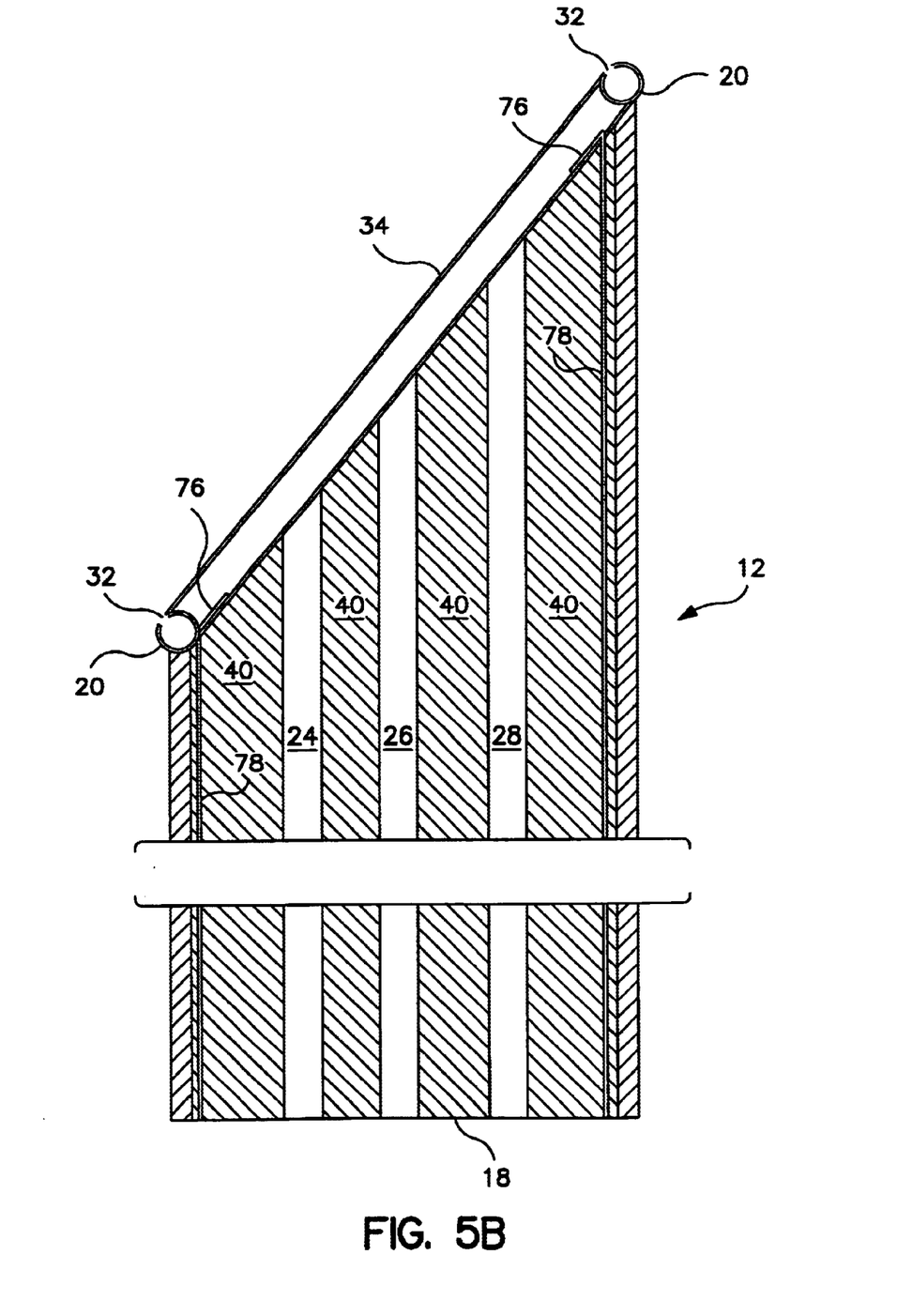
FIG. 5B is a cross-sectional view taken along substantially along line 5—5 in FIG. 3 and showing a second alternative construction of the catheter distal end.
Figure 6:
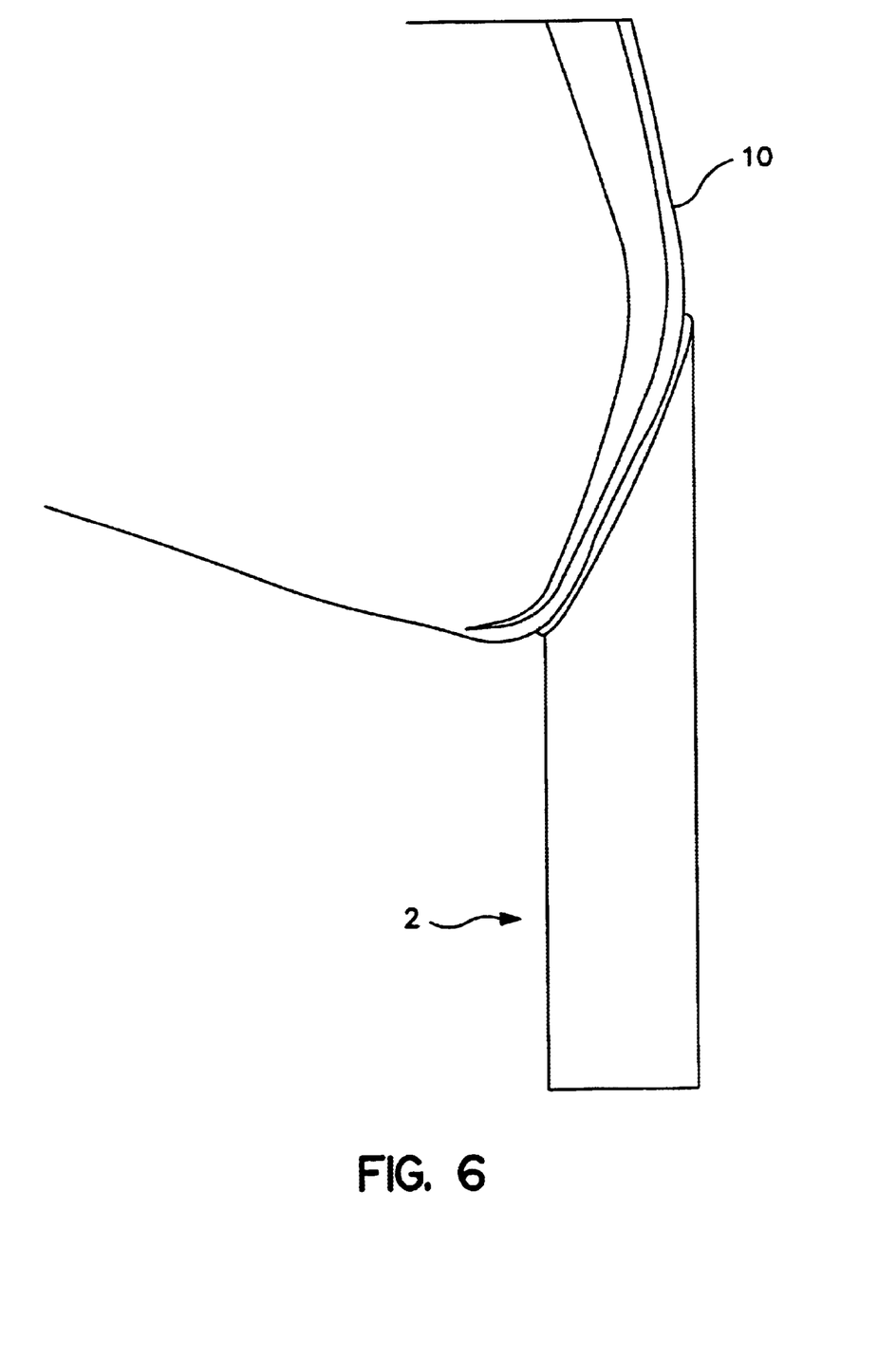
FIG. 6 is a perspective view showing the injection apparatus of FIG. 1 attached to a myocardium.

The tubular wall 14 includes an end face 30 of the tubular wall 14 that is formed at an oblique angle relative to the longitudinal axis 22 in order to facilitate placement of the catheter distal end 20 against the myocardium 10. As can be seen in FIGS. 2, 5A and 5B, the catheter distal end 20 is also provided with plural suction elements 32 that are adapted to facilitate the aforementioned suction attachment of the catheter 12 to the myocardium 10. The geometry of this attachment is illustrated in FIG. 6. In FIGS. 2 and 5A, the suction elements 32 are formed as a plurality of openings located in spaced relation around the tubular wall end face 30. In FIG. 5B, the suction elements 32 are formed as a plurality of openings located in spaced relation around a tubular ring member 34 that is mounted at the catheter distal end 20, preferably on the tubular wall end face 30. As briefly mentioned above, the ring member 34 is made from a material that is suitably soft and compliant to enable the catheter 12 to easily conform and attach to the surface of the myocardium 10 in the event that the catheter distal end 20 is itself too stiff and unyielding. Note, however, that the ring member 34 must at the same time be sufficiently stiff to deliver a vacuum to the myocardium 10. One proposed material that should provide these requisite properties is a flexible braided or fabric sheet having stiffening members therein as needed to deliver the required vacuum to the suction elements 32. Note that the plurality of openings formed in the ring member 34 are located in spaced relation around an exposed face of the ring member, and extend generally parallel to the catheter longitudinal axis 22.

Figure 4A:
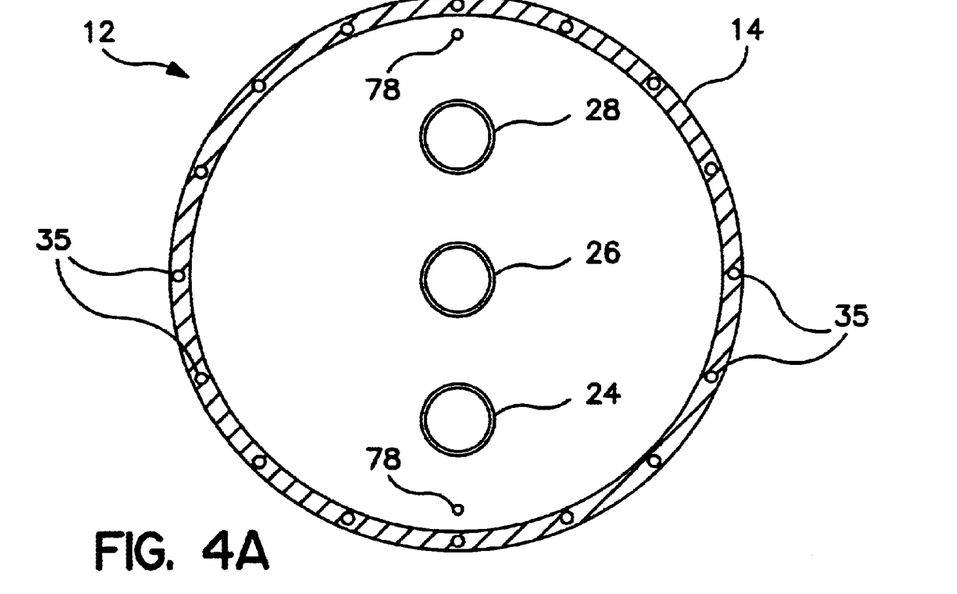
FIG. 4A is a cross-sectional view taken substantially along line 4—4 in FIG. 2 and showing a first alternative catheter construction.
Figure 4B:
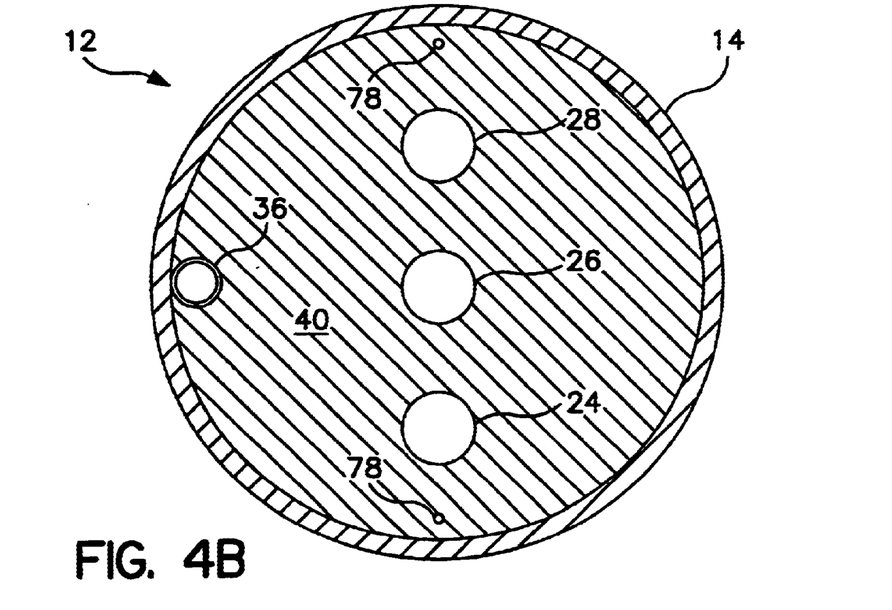
FIG. 4B is a cross-sectional view taken substantially along line 4—4 in FIG. 2 and showing a second alternative catheter construction.

As shown in FIGS. 4A and 5A, the plural suction elements 32, whether formed in the tubular wall end face 30 or in the ring member 34, can be respectively connected to plural corresponding vacuum passages 35 that extend in the tubular wall 14 from the catheter distal end 20 to the catheter base end 18. Alternatively, as shown in FIGS. 4B and 5B, the suction elements 32, whether formed in the tubular wall end face 30 or in the ring member 34, can be connected to a single vacuum passage 36 that extends from the catheter distal end 20 to the catheter base end 18. A suitable vacuum source (not shown) is provided at the catheter base end 18 for attachment to either the plural vacuum passages 34, or the single vacuum passage 36, in order to deliver the required vacuum to the suction elements 32.

With continuing reference now to FIGS. 2–5B, plural lumena, namely, a lumen 24, a lumen 26 and a lumen 28, extend from the catheter base end 18 to the catheter distal end 20 within the catheter interior 16. The lumena 24, 26 and 28 can be formed in several ways depending on the construction details of the catheter 12. In that regard, one construction alternative for the catheter 12 is to make the catheter interior 16 hollow, as shown in FIGS. 4A and 5A. In this configuration, the lumena 24, 26 and 28 can be made from plastic tubes. To secure and position each such tube at the catheter distal end 20, a flat cover member 38 can be mounted thereto, as shown in FIG. 5A. The cover member 38 has apertures that respectively receive or otherwise mount one of the lumena 24, 26 and 28. Alternatively, the catheter interior may be filled with a solid core 40, as shown in FIGS. 4B and 5B. In this configuration, the lumena can be implemented as longitudinal bores formed in the solid core 40, or they may be implemented as plastic tubes that extend through such bores.

Figure 5C:
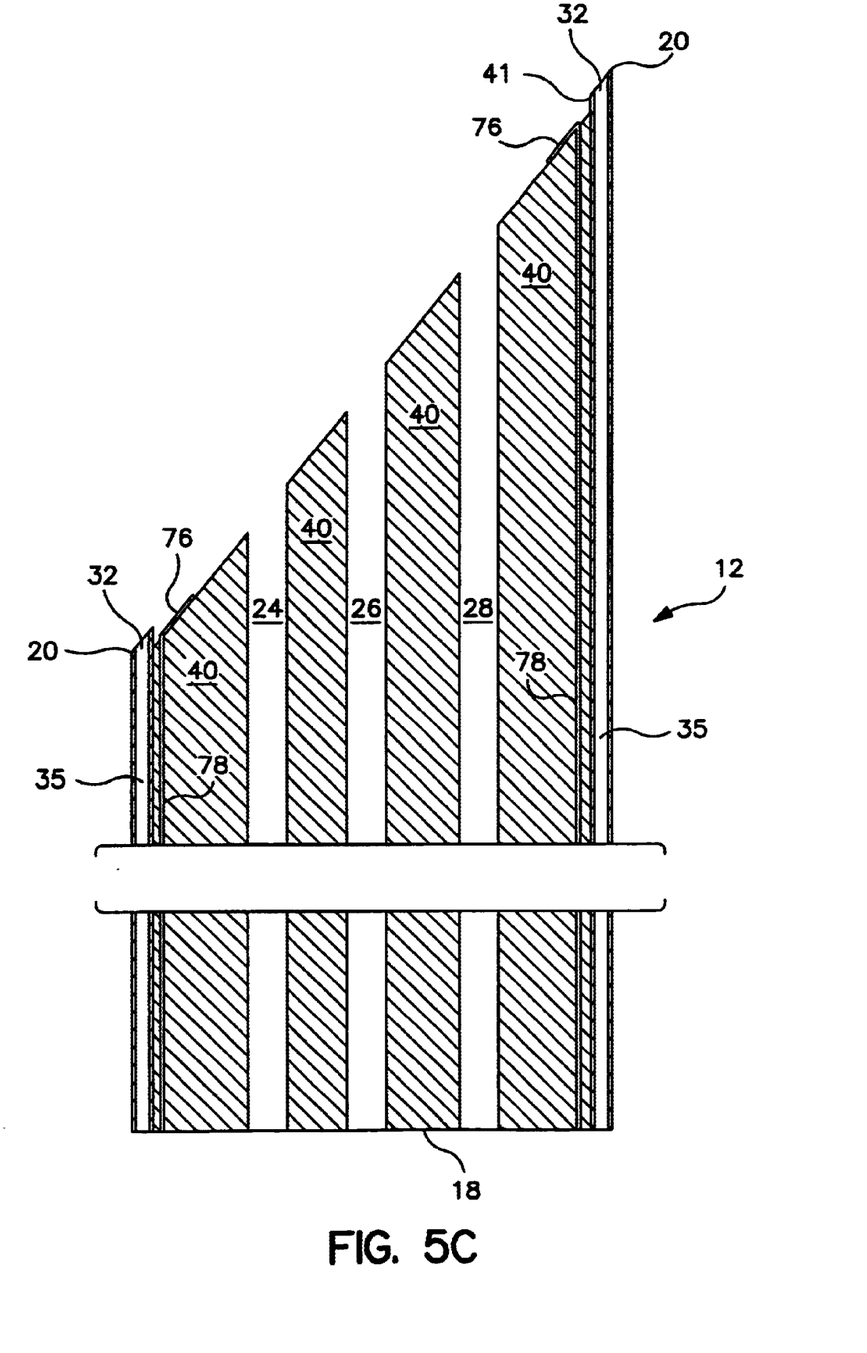
FIG. 5C is a cross-sectional view taken along substantially along line 5—5 in FIG. 3 and showing a third alternative construction of the catheter distal end.

An advantage provided by use of the solid core 40 is that the core material can be selected to provide the stiffness required by the catheter 12, while the catheter wall 14 is made from a relatively soft and compliant material. By extending the catheter wall 14 a short distance (e.g., about 1 mm.) beyond the distal end of the solid core 40, a soft cushion (see element 41 in FIG. 5C) will be formed at the catheter distal end 20 to facilitate compliance with the surface of the myocardium 20.

Figure 7:
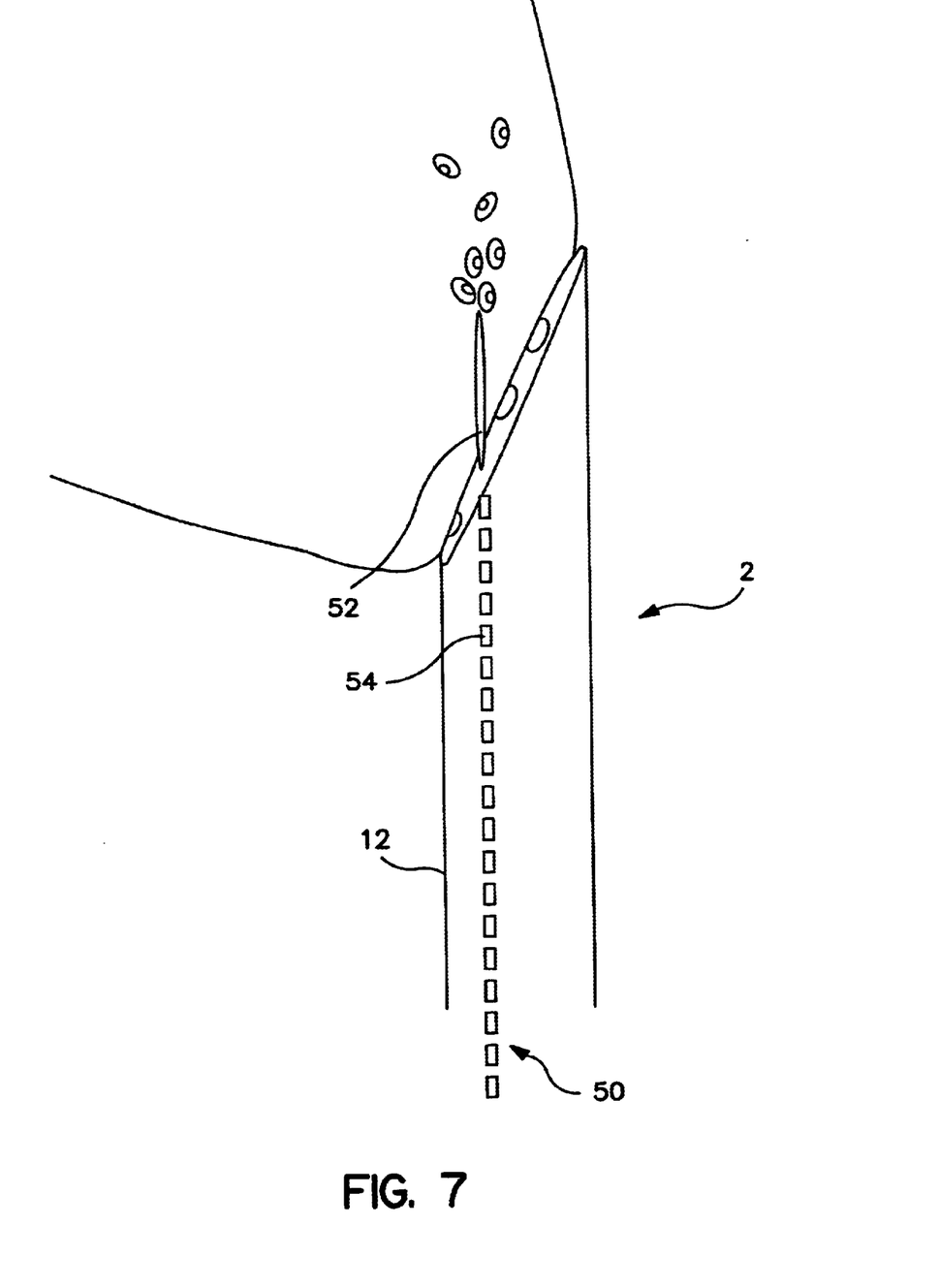
FIG. 7 is a perspective view showing the injection of material into a myocardium using a syringe carried by the injection apparatus of FIG. 1.

The lumena 24, 26 and 28 are used to carry various functional devices of the injection apparatus 2. As shown in FIG. 7, one of the lumena, e.g., lumen 24, can be used to slidably receive and support an elongated syringe 50 having a stainless steel needle tip 52 and an extendable/retractable catheter 54. The catheter 54 runs from the catheter distal end 20 to the catheter base end 18, and can be manipulated between a retracted position wherein the needle tip 52 is recessed within the catheter interior 16, to an extended position wherein the needle tip extends from the catheter interior. The injection apparatus 50 is used to introduce a myocardial repair or treatment material into a dysfunctional area of the myocardium 10 while the catheter distal end 20 is attached thereto. This is accomplished by extending the needle tip 52 into the myocardium, introducing the myocardial repair or treatment material into the catheter 54, and injecting it via the needle tip 52 into the dysfunctional area.

Figure 8:
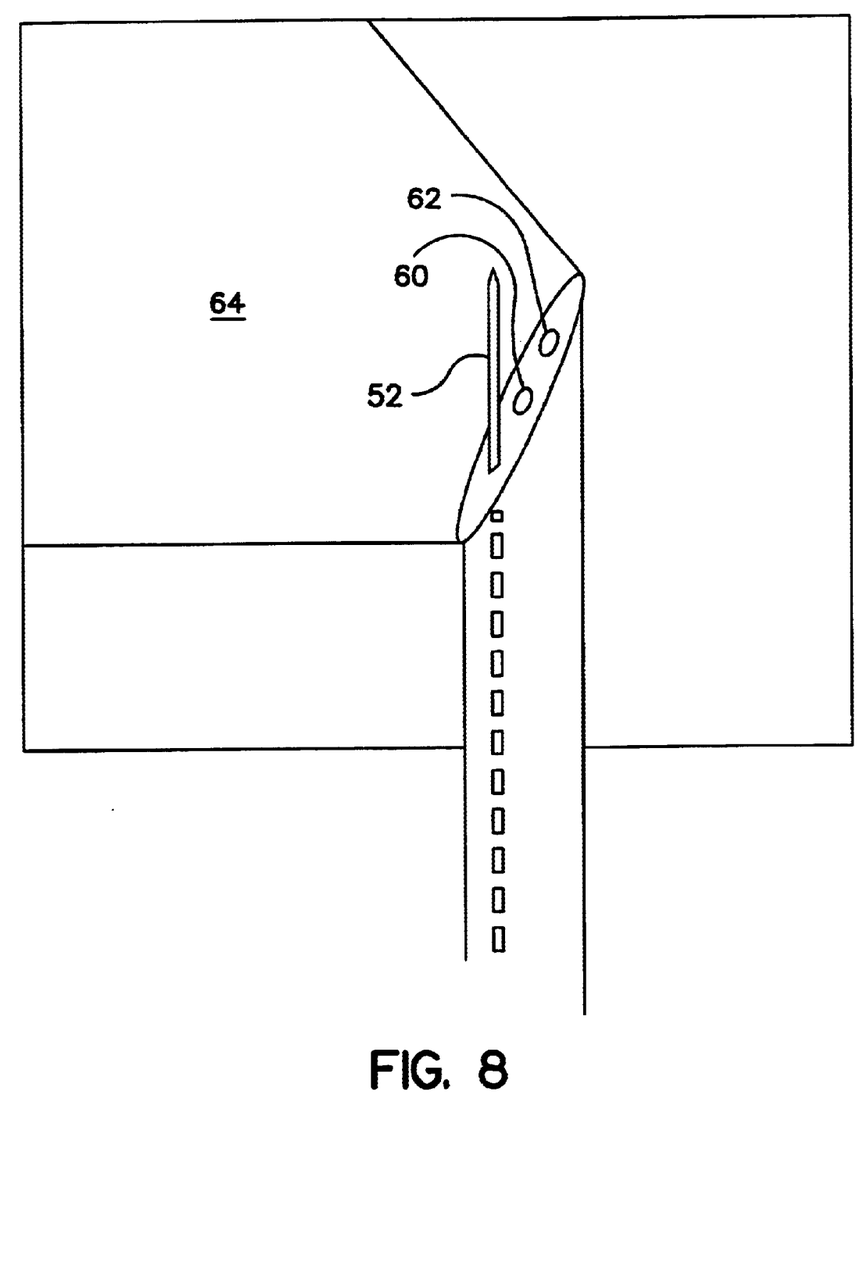
FIG. 8 is a perspective view showing the use of a optical imaging system and an ultrasound imaging device carried by the injection apparatus of FIG. 1.

As shown in FIG. 8, one of the lumena, e.g., lumen 26, can be used to slidably receive and support an optical imaging system 60, while another one of the lumena, e.g., lumen 28, can be used to slidably receive and support an ultrasound imaging device 62. The optical imaging system 60 includes an integrated light source for providing illumination 64 and a camera that is in communication with a remote image viewing system (not shown). Advantageously, by using the optical imaging system 60, the catheter can be self-guided to a selected area of the myocardium 10 without X-ray imaging. Additionally, ultrasound imaging using the ultrasound imaging device 62 can be activated to appraise ventricular motility.

Figure 9A:
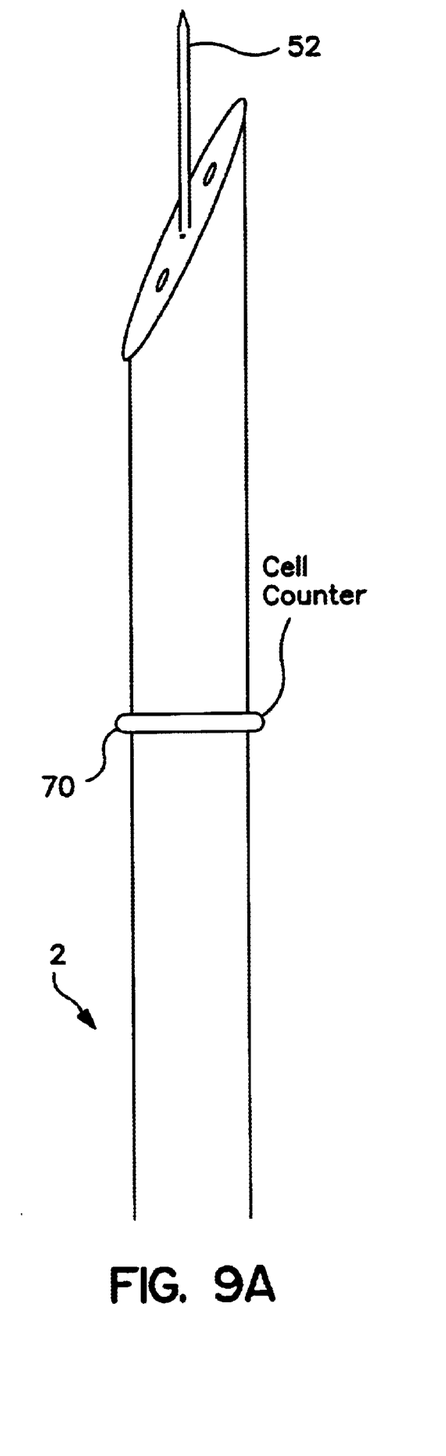
FIG. 9A is a perspective view showing the use of a cell counter carried by the injection apparatus of FIG. 1.
Figure 9B:
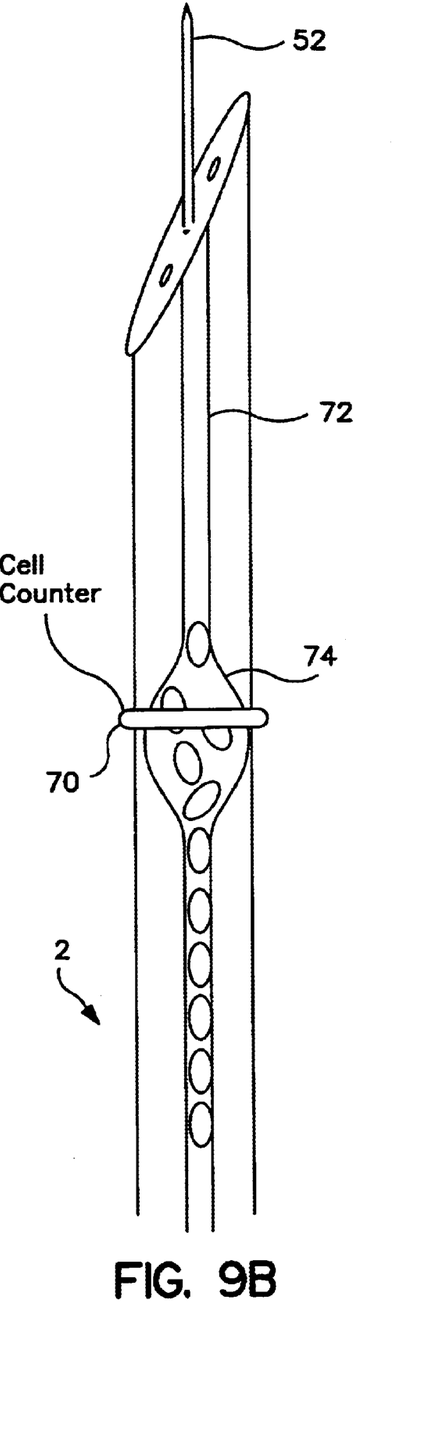
FIG. 9B is a perspective view similar to FIG. 9A but with the injection apparatus being partially transparent to better illustrate the operation of the cell counter.

As shown in FIGS. 9A and 9B, a further function supported by the injection apparatus 2 is the use of a cell counter 70. This conventional device can be mounted to the outside of the catheter 12. As shown in FIG. 9B, the syringe 50 also uses a modified catheter 72 having an enlarged area 74 in the vicinity of the cell counter 70. Although not shown, the cell counter 70 communicates with remote equipment that can be monitored by the medical practitioner to determine when to terminate cell implantation treatment at a given area of the myocardium 10.

A further functional enhancement to the injection apparatus 2 is the use pair of EKG electrodes 76 (see FIGS. 3, 5A and 5B) that are mounted at the catheter distal end 20. These electrodes are electrically connected via leads 78 to remote EKG monitoring equipment (not shown) that can be used to monitor myocardial electrical activity during use of the injection apparatus 2.

Figure 10:
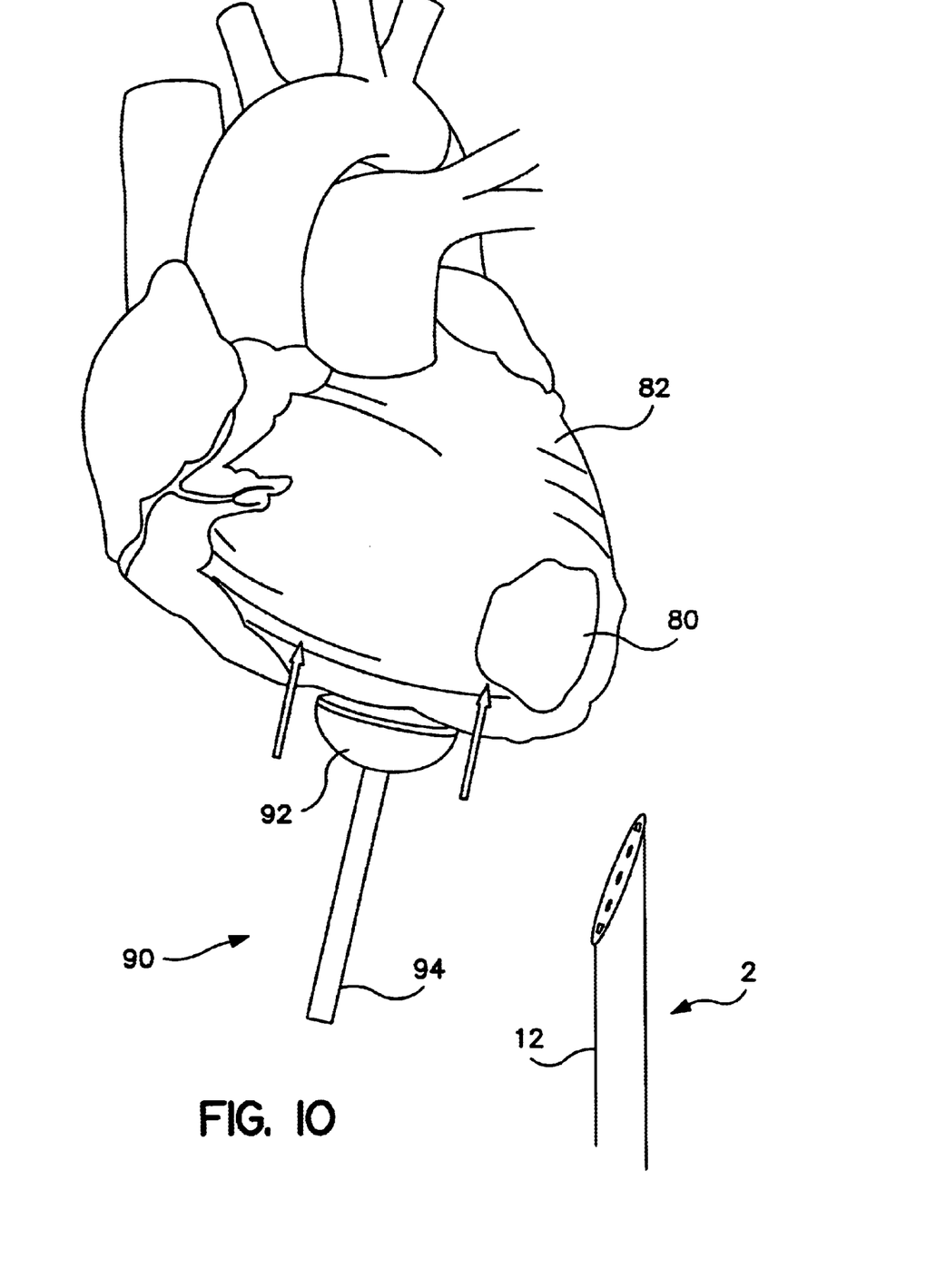
FIG. 10 is a perspective view showing a first portion of a method for performing myocardial repair or treatment using the injection apparatus of FIG. 1 in which a patient's heart has been elevated using a hydraulic suction device in order to present a damaged area thereof for access by the injection apparatus.
Figure 11A:
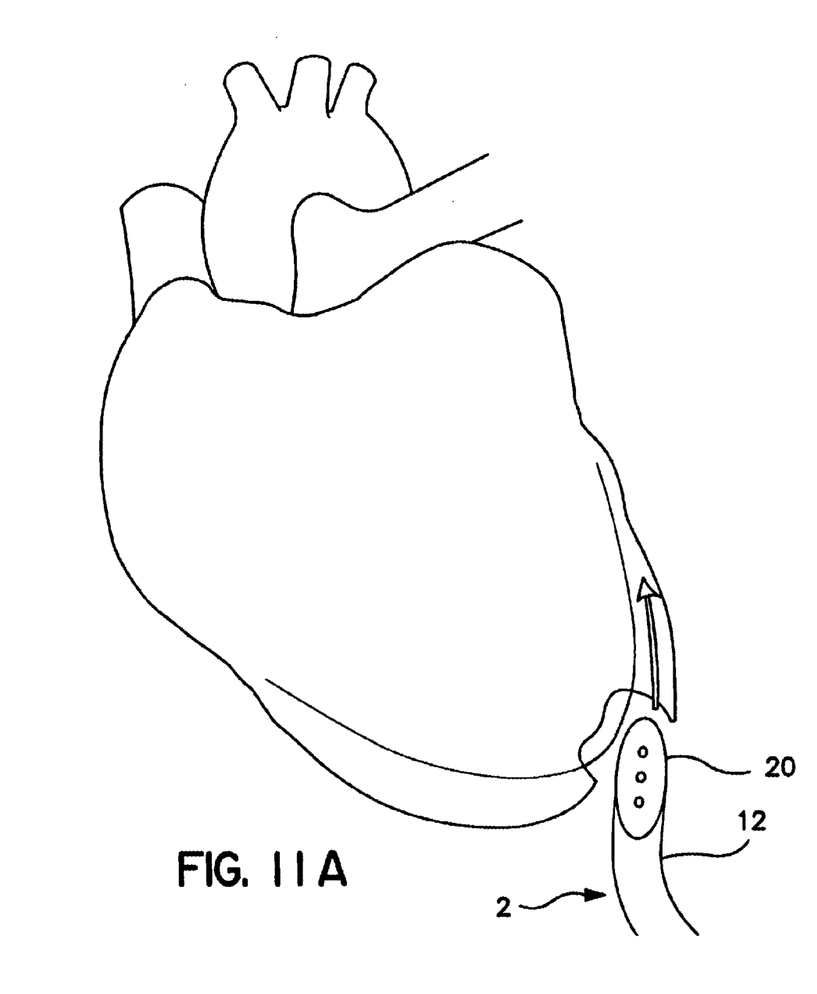
FIG. 11A is perspective view showing a second portion of a method for performing myocardial repair or treatment using the injection apparatus of FIG. 1 in which the distal end of the injection apparatus enters an opening in a dilated pericardial sac.
Figure 11B:
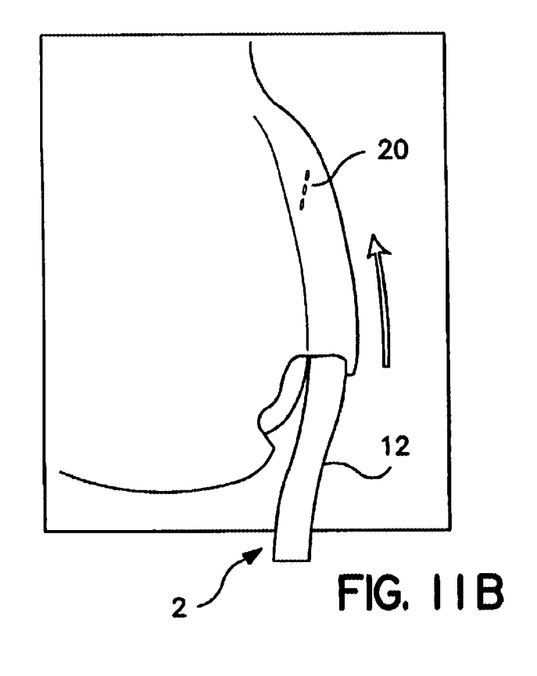
FIG. 11B is a perspective view similar to FIG. 11A in which the distal end of injection apparatus has progressed further into the dilated pericardial sac.
Figure 12:
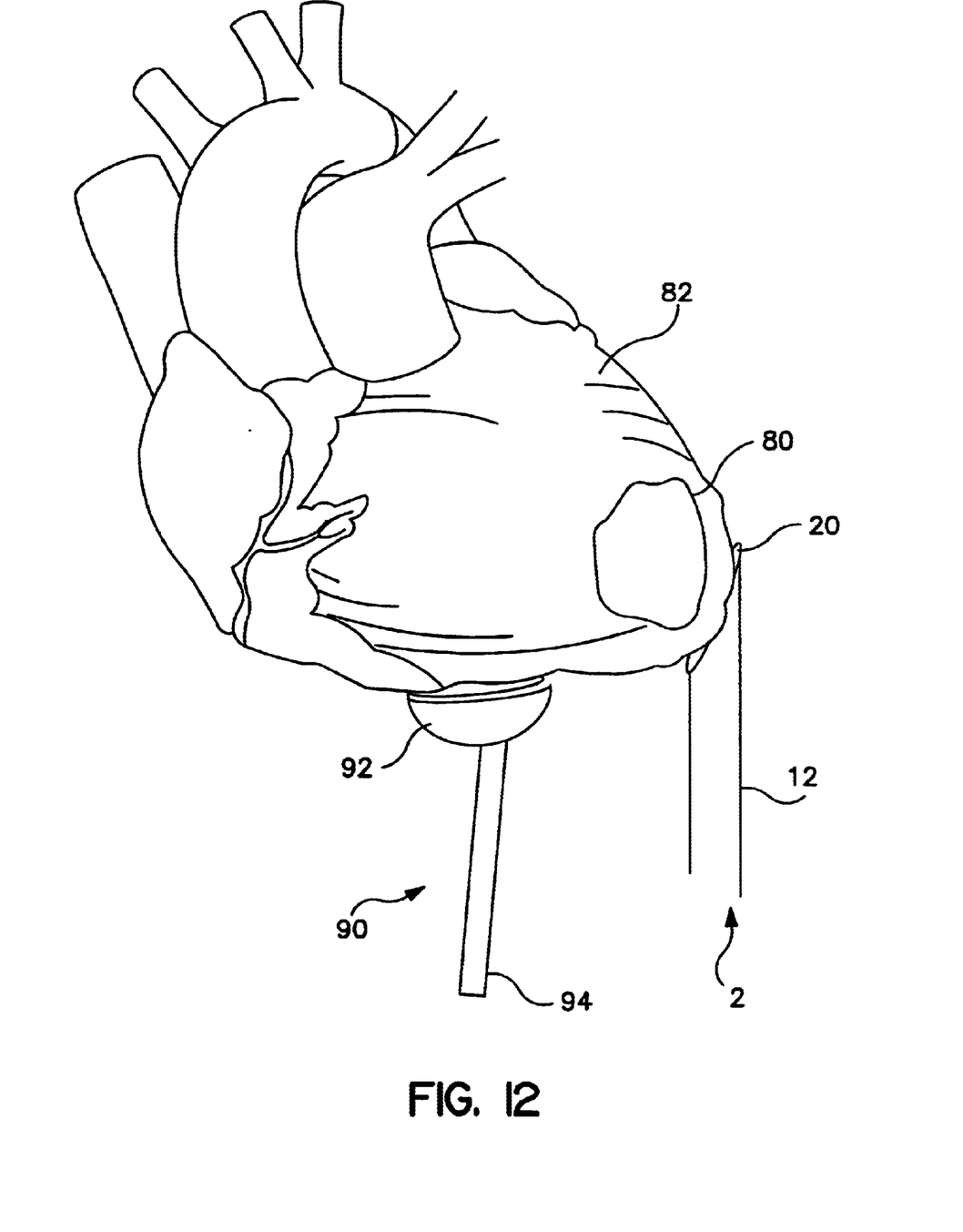
FIG. 12 is a perspective view showing a third portion of a method for performing myocardial repair or treatment using the injection apparatus of FIG. 1 in which the injection apparatus is attached to the myocardium adjacent the damaged area thereof.

Turning now to FIGS. 10–12, a procedure for percutaneous epicardial injection will now be described wherein the injection apparatus 2 is used to introduce a myocardial repair or treatment area into a damaged myocardium area 80 of a heart 82. To commence the procedure, a medical practitioner prepares an opening beneath the patient's xiphoid bone using local anesthesia and routine preparation. Through this opening, a small needle is inserted into the patient's pericardium, followed by a guide wire and balloon dilator (not shown) which are introduced into the pericardial sac. The pericardial sac is then dilated. If necessary to expose the damaged area 80 of the myocardium 82, an introducer 90, having a suction cup 92 mounted to the end of a hydraulic sheath 94 is introduced into the dilated pericardial sac. Advancement of the suction cup 92 and the hydraulic sheath 94 while manipulating the introducer 90 brings the suction cup into contact with the ventricular apex of the heart 82 (see FIG. 10). Hydraulic suction may then be applied to elevate the heart 82 as necessary.

After selecting the injection apparatus 2 and preparing it for use, the medical practitioner introduces the catheter 12 through the above-mentioned sub-xiphoidal opening and guides the catheter distal end 20 into the pericardial sac. This is shown in FIGS. 11A and 11B. The catheter 12 is manipulated until the distal end 20 is located adjacent the damaged area 80. As previously indicated, the catheter 12 can be self-guided to the damaged area 80 without X-ray imaging using the optical imaging system 60. As also noted, the ultrasound imaging device 62 can be used to appraise ventricular motility. When the damaged area 80 is identified, the catheter distal end 20 is attached to the myocardium with the aid of its oblique tubular wall end face 30 and associated suction elements 32. The needle tip 52 of the syringe 50 is now extended into the damaged area 80 and the repair or treatment material is injected therein. If cells are being injected, the cell counter 70 may be used to determine the amount of material being introduced. The EKG electrodes 76 may likewise be used to monitor myocardial electrical activity. Following material injection as described above, the injection apparatus 2 may be detached from the heart 82 and repositioned at other areas thereof. The injection procedure may then be repeated, as many times as necessary, until all affected areas of the heart are repaired or treated.

Accordingly, an apparatus and method for percutaneous epicardial injection have been disclosed. While various embodiments of the invention have been shown and described, it should be apparent that many variations and alternative embodiments could be implemented in accordance with the invention. For example, rather than using a syringe 50 with a single needle tip, a syringe with multiple needle tips could be used to apply a repair or treatment material to a larger area. Similarly, multiple syringes could be used. It is understood, therefore, that the invention is not to be in any way limited except in accordance with the spirit of the appended claims and their equivalents.

What is claimed is:

1. A percutaneous epicardial injection apparatus for myocardial repair and treatment, comprising:
    a catheter having a tubular wall, an interior portion surrounded by said tubular wall, a base end, a distal end and a central longitudinal axis extending between said catheter base end and said catheter distal end;
    said catheter distal end being adapted to attach to a myocardium;
    a lumen extending from said catheter base end to said catheter distal end within said catheter interior, said lumen being adapted to slidably support an elongated syringe having a needle tip adapted for movement between a retracted position wherein said needle tip is recessed within said catheter interior to an extended position wherein said needle tip extends from said catheter interior; and
    said catheter distal end having a tubular wall end face formed with a plurality of openings located in spaced relation around said end face and defining suction elements adapted to facilitate attachment of said catheter to said myocardium;
    whereby said injection apparatus may be used to introduce a myocardial repair or treatment material into a dysfunctional area of said myocardium while said catheter distal end is attached thereto by extending said needle tip into said myocardium and injecting the myocardial repair or treatment material into said dysfunctional area.

2. A percutaneous epicardial injection apparatus in accordance with claim 1 wherein said end face of said tubular wall is formed at an oblique angle relative to said catheter longitudinal axis.

3. A percutaneous epicardial injection apparatus in accordance with claim 1 wherein said suction elements are respectively connected to vacuum passages extending in said tubular wall from said catheter distal end to said catheter base end.

4. A percutaneous epicardial injection apparatus in accordance with claim 1 wherein said suction elements are connected to a single vacuum passage extending in said catheter interior from said catheter distal end to said catheter base end.

5. A percutaneous epicardial injection apparatus in accordance with claim 1 further including a lumen extending from said catheter base end to said catheter distal end within said catheter interior, and carrying an optical imaging system.

6. A percutaneous epicardial injection apparatus in accordance with claim 1 further including a lumen extending from said catheter base end to said catheter distal end within said catheter interior, and carrying an ultrasound imaging device.

7. A percutaneous epicardial injection apparatus in accordance with claim 1 further including a air of electrodes mounted at said catheter distal end for myocardial electrical monitoring.

8. A percutaneous epicardial injection apparatus in accordance with claim 1 wherein said catheter interior is hollow and said catheter includes a cover member mounted on said tubular wall at said catheter distal end, said cover member being perforated to receive said lumen.

9. A percutaneous epicardial injection apparatus in accordance with claim 1 wherein said catheter interior is solid filled and perforated to provide or receive said lumen.

10. A Percutaneous epicardial injection apparatus for myocardial repair and treatment, comprising:
    a catheter having a tubular wall, an interior portion surrounded by said tubular wall, a base end, a distal end and a central longitudinal axis extending between said catheter base end and said catheter distal end;
    said catheter distal end being adapted to attach to a myocardium;
    a lumen extending from said catheter base end to said catheter distal end within said catheter interior, said lumen being adapted to slidably support an elongated syringe having a needle tip adapted for movement between a retracted position wherein said needle tip is recessed within said catheter interior to an extended position wherein said needle tip extends from said catheter interior;
    said catheter distal end including an end face of said tubular wall that is formed at an oblique angle relative to said catheter longitudinal axis;
    said catheter distal end further including suction elements adapted to facilitate attachment of said catheter to said myocardium; and
    said suction elements comprising a plurality of openings in a compliant tubular ring member mounted at said catheter distal end;
    whereby said injection apparatus may be used to introduce a myocardial repair or treatment material into a dysfunctional area of said myocardium while said catheter distal end is attached thereto by extending said needle tip into said myocardium and injecting the myocardial repair or treatment material into dysfunctional area.

11. A percutaneous epicardial injection apparatus in accordance with claim 10 wherein said plurality of opening are located in spaced relation around an exposed face of said tubular member and extend generally parallel to said catheter longitudinal axis.

12. A percutaneous epicardial injection apparatus in accordance with claim 11 wherein said tubular member is connected to a vacuum passage in fluid communication with said plurality of openings and extending from said tubular member to said catheter base end.

13. A percutaneous epicardial injection apparatus for myocardial repair and treatment, comprising:

a catheter having a tubular wall, an interior portion surrounded by said tubular wall, a base end, a distal end and a central longitudinal axis extending between said catheter base end and said catheter distal end;

said catheter distal end being adapted to attach to a myocardium;

a lumen extending from said catheter base end to said catheter distal end within said catheter interior, said lumen being adapted to slidably support an elongated syringe having a needle tip adapted for movement between a retracted position wherein said needle tip is recessed within said catheter interior to an extended position wherein said needle tip is recessed catheter interior; and a cell counter mounted on said tubular wall;

whereby said injection apparatus mat be used to introduce a myocardium repair or treatment material into a dysfunctional area of said myocardium while said catheter distal end is attached thereto by extending said needle tip into said myocardium and injecting the myocardial repair or treatment material into said dysfunctional area.

14. A method for applying a myocardial repair or treatment material to a myocardium, comprising the steps of:

via percutaneous approach beneath the xiphoid bone of a patient, inserting a small needle patient's pericardium;

introducing a guide wire and balloon dilator into the patient's pericardial sac;

dilating the patient's pericardial sac;

following elevation of the patient's heart as necessary, selecting a percutaneous epicardial injection apparatus and preparing it for use;

said percutaneous epicardial injection apparatus comprising:

a catheter having a tubular wall, an interior portion surrounded by said tubular wall, a base end, a distal end and a central longitudinal axis extending between said catheter base end and said catheter distal end;

said catheter distal end being adapted to attach to a myocardium; and a lumen extending from said catheter base end to said catheter distal end within said catheter interior, said lumen being adapted to slidably support an elongated syringe having a needle tip adapted for movement between a retracted position wherein said needle tip is recessed within said catheter interior to an extended position wherein said needle tip extends from said catheter interior;

whereby said injection apparatus may be used to introduce a myocardial repair or treatment material into a dysfunctional area of said myocardium while said catheter distal end is attached thereto by extending said needle tip into said myocardium and injecting the myocardial repair or treatment material into said dysfunctional area;

introducing said catheter using a percutaneous approach and guiding said catheter into said pericardial sac to a selected area of the patient's myocardium;

attaching said catheter distal end to said myocardium at said selected area;

extending said needle tip of said syringe into said selected area; and injecting said repair or treatment material into said myocardium.

15. A method in accordance with claim 14 wherein said injection apparatus includes an optical imaging system and said guiding step includes using said optical imaging system to guide said catheter to said selected area.

16. A method in accordance with claim 14 wherein said injection apparatus includes an ultrasound imaging device and said guiding step includes using said ultrasound imaging device to guide said catheter to said selected area.

17. A method in accordance with claim 14 wherein said injection apparatus includes a pair of electrodes and said method includes using said electrodes to monitor electrical activity of said myocardium.

18. A percutaneous epicardial injection apparatus for myocardial repair and treatment, comprising:

a catheter having a tubular wall, an interior portion surrounded by said tubular wall, a base end, a distal end and a central longitudinal axis extending between said catheter base end and said catheter distal end;

said catheter distal end being adapted to attach to a myocardium and including an end face of said tubular wall that is formed at an oblique angle relative to said catheter longitudinal axis;

said catheter distal end further including suction means for facilitating attachment of said catheter to said myocardium;

a first lumen extending from said catheter base end to said catheter distal end within said catheter interior, said lumen being adapted to slidably support an elongated syringe having a needle tip adapted for movement between a retracted position wherein said needle tip is recessed within said catheter interior to an extended position wherein said needle tip extends from said catheter interior;

a second lumen extending from said catheter base end to said catheter distal end within said catheter interior, and carrying an optical imaging device that includes a light source;

a third lumen extending from said catheter base end to said catheter distal end within said catheter interior, and carrying an ultrasound imaging device;

a cell counter mounted on said tubular wall; and a pair of electrodes mounted at said catheter distal end for myocardial electrical monitoring;

whereby said injection apparatus may be used to introduce a myocardial repair or treatment material into a dysfunctional area of said myocardium while said distal end is attached thereto by extending said needle tip of said syringe into said myocardium and injecting the myocardial repair or treatment material into said dysfunctional area.

* * * * *